(12) United States Patent
Harris et al.

(10) Patent No.: US 7,166,304 B2
(45) Date of Patent: *Jan. 23, 2007

(54) DEGRADABLE HETEROBIFUNCTIONAL POLY(ETHYLENE GLYCOL) ACRYLATES

(75) Inventors: J. Milton Harris, Huntsville, AL (US); Xuan Zhao, Huntsville, AL (US)

(73) Assignee: Debio Recherche Pharmaceutique S.A., Martigny (CH)

( * ) Notice: Subject to any disclaimer, the term of this patent is extended or adjusted under 35 U.S.C. 154(b) by 456 days.

This patent is subject to a terminal disclaimer.

(21) Appl. No.: 10/684,946

(22) Filed: Oct. 14, 2003

(65) Prior Publication Data
US 2004/0086992 A1    May 6, 2004

Related U.S. Application Data

(60) Continuation of application No. 09/824,395, filed on Apr. 2, 2001, now abandoned, which is a division of application No. 09/226,341, filed on Jan. 6, 1999, now Pat. No. 6,362,276.

(60) Provisional application No. 60/070,680, filed on Jan. 7, 1998.

(51) Int. Cl.
*A61K 9/00* (2006.01)
*A61K 47/48* (2006.01)
*C12N 11/00* (2006.01)
*G01N 33/543* (2006.01)
*C07K 17/00* (2006.01)

(52) U.S. Cl. ............ 424/487; 435/174; 435/181; 436/518; 436/532; 525/54.1; 530/402; 530/810; 530/816

(58) Field of Classification Search .......... None
See application file for complete search history.

(56) References Cited

U.S. PATENT DOCUMENTS

| | | | |
|---|---|---|---|
| 3,419,006 A | 12/1968 | King | |
| 3,963,805 A | 6/1976 | Chu | |
| 4,179,337 A | 12/1979 | Davis et al. | |
| 4,424,311 A | 1/1984 | Nagaoka et al. | |
| 4,670,417 A | 6/1987 | Iwasaki et al. | |
| 4,894,238 A | 1/1990 | Embry et al. | |
| 5,410,016 A | 4/1995 | Hubbell et al. | |
| 5,550,178 A | 8/1996 | Desai et al. | |
| 5,626,863 A | 5/1997 | Hubbell et al. | |
| 5,648,506 A | 7/1997 | Desai et al. | |
| 5,840,900 A | 11/1998 | Greenwald et al. | |
| 5,977,277 A | 11/1999 | Yokoyama et al. | |
| 6,448,369 B1 * | 9/2002 | Bentley et al. | 528/425 |
| 6,946,499 B1 * | 9/2005 | Loomis et al. | 523/105 |

FOREIGN PATENT DOCUMENTS

| | | |
|---|---|---|
| EP | 0 658 585 | 6/1995 |
| WO | WO 96/20012 | 7/1996 |
| WO | WO 97/05185 | 2/1997 |
| WO | WO 99/07417 | 2/1999 |

OTHER PUBLICATIONS

J.M. Harris, Ed., "Biomedical and Biotechnical Applications of Poly(Ethylene Glycol) Chemistry", Plenum, New York, 1992.
Greenwald et al., Highly Water Soluble Taxol Derivatives: 7-Polyethylene Glycol Carbamates and Carbonates:, *J. Org. Chem.*, vol. 60, No. 2, pp. 331-336, 1995.
Sawhney et al., "Biorodible Hydrogels Based on Photopolymerized Poly(Ethylene Glycol)-co-poly(α-hydroxy acid) Diacrylate Macromers", *Macromolecules*, vol. 26, No. 4, pp. 581-587 (1993).
Gayet et al., "High Water Content BSA-PEG Hydrogel for Controlled Release Device: Evaluation of the Drug Release Properties", *Journal of Controlled Release 38*, pp. 177-184 (1996).
Yang et al., "Activity and Stability of Enzymes Incorporated into Acrylic Polymers," *J. Am. Chem Soc.*, 117, pp. 4843-4850 (1995).

* cited by examiner

*Primary Examiner*—David M. Naff
(74) *Attorney, Agent, or Firm*—Alston & Bird LLP

(57) ABSTRACT

A heterobifunctional poly(ethylene glycol) is provided having a hydrolytically degradable linkage, a first terminus comprising an acrylate group, and a second terminus comprising a target such as a protein or pharmaceutical agent or a reactive moiety capable of coupling to a target. Hydrogels can be prepared. The hydrogels can be used as a carrier for a protein or a pharmaceutical agent that can be readily released in a controlled fashion.

4 Claims, 1 Drawing Sheet

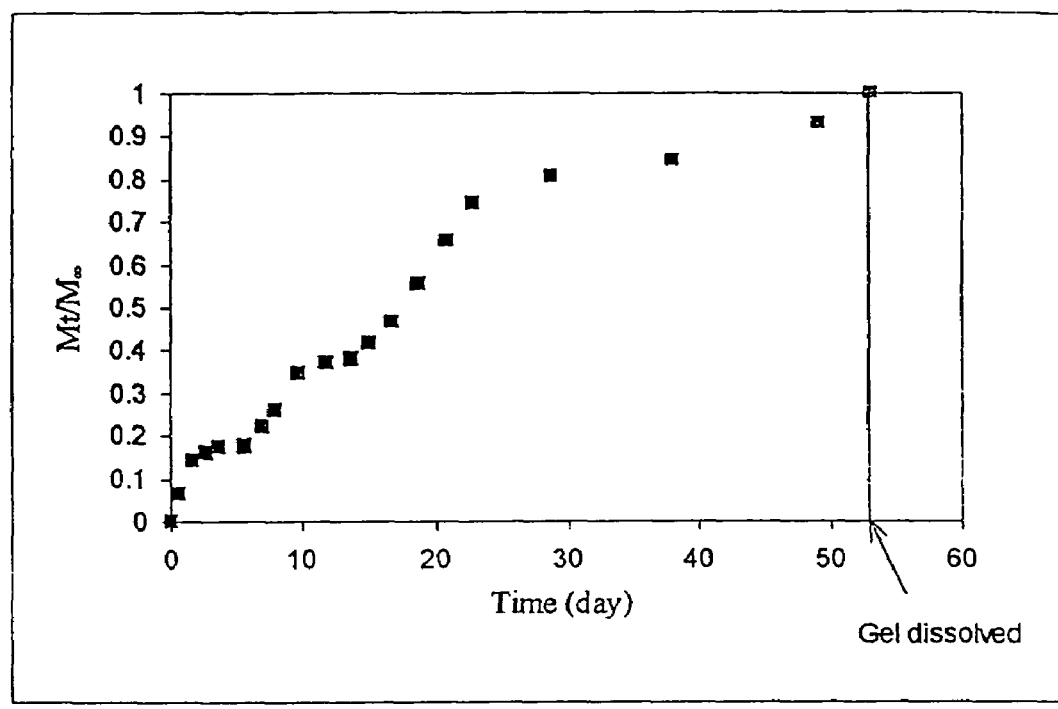
Figure 1. Release profile of lucifer-yellow lysozyme from a PEG acrylate hydrogel.

DEGRADABLE HETEROBIFUNCTIONAL POLY(ETHYLENE GLYCOL) ACRYLATES

CROSS REFERENCE TO RELATED APPLICATION

This application is a continuation application of application Ser. No. 09/824,395, filed Apr. 2, 2001, now abandoned which is a divisional application of application Ser. No. 09/226,341, filed Jan. 6, 1999 now U.S. Pat. No. 6,362,276, which is related to commonly owned copending Provisional Application Ser. No. 60/070,680, filed Jan. 7, 1998, incorporated by reference in its entirety, and claims the benefit of its filing date under 35 USC Section 119(e).

FIELD OF THE INVENTION

This invention relates to heterobifunctional poly(alkylene oxides) having degradable linkages and to conjugates derived therefrom.

BACKGROUND OF THE INVENTION

In its most common form, the poly(alkylene oxide) poly (ethylene glycol) (PEG) is a linear polymer terminated at each end with hydroxyl groups:

$$HO-CH_2CH_2O-(CH_2CH_2O)_n-CH_2CH_2-OH$$

This polymer can be represented in a brief form as HO-PEG-OH where it is understood that -PEG- represents the following structural unit:

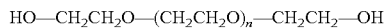

where n typically ranges from approximately 10 to 2000.

PEG is of great utility in a variety of biotechnical and pharmaceutical applications, particularly for drug delivery and modification of drug surfaces to promote nonfouling characteristics.

PEG is not toxic, does not tend to promote an immune response, and is soluble in water and in many organic solvents. The PEG polymer can be covalently attached to insoluble molecules to make the resulting PEG-molecule conjugate soluble. For example, Greenwald, Pendri and Bolikal in *J. Org. Chem.*, 60, 331–336 (1995) recite that the water-insoluble drug taxol, when coupled to PEG, becomes water soluble. Davis et al. in U.S. Pat. No. 4,179,337 recite that proteins coupled to PEG have an enhanced blood circulation lifetime because of a reduced rate of kidney clearance and reduced immunogenicity. The lack of toxicity of the polymer and its rate of clearance from the body are important considerations in pharmaceutical applications. Pharmaceutical applications and many leading references are described in the book by Harris (J. M. Harris, Ed., "Biomedical and Biotechnical Applications of Polyethylene Glycol Chemistry, Plenum, New York, 1992).

PEG is commonly used as methoxy-PEG-OH, or mPEG in brief, in which one terminus is the relatively inert methoxy group, while the other terminus is a hydroxyl group that is subject to ready chemical modification

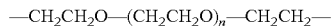

PEG is also commonly used in branched forms that can be prepared by addition of ethylene oxide to various polyols, including glycerol, pentaerythritol and sorbitol. For example, the four-armed branched PEG prepared from pentaerythritol is shown below:

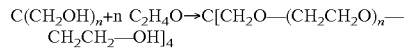

The branched PEGs can be represented in a general form as R(-PEG-OH)$_n$ in which R represents the central core molecule, which can include, e.g., glycerol or pentaerythritol, and n represents the number of arms.

Often it is necessary to use an "activated derivative" of PEG to couple PEG to a molecule. The hydroxyl group located at the PEG terminus, or other group subject to ready chemical modification, is activated by modifying or replacing the group with a functional group suitable for reacting with a group on another molecule, including, e.g., proteins, surfaces, enzymes, and others. For example, the succinimidyl "active ester" of carboxymethylated PEG forms covalent bonds with amino groups on proteins as described by K. Iwasaki and Y. Iwashita in U.S. Pat. No. 4,670,417. The synthesis described in U.S. Pat. No. 4,670,417 is illustrated below with the active ester reacting with amino groups of a protein in which the succinimidyl group is represented as NHS and the protein is represented as PRO-NH$_2$:

Succinimidyl "active esters", such as PEG-OCH$_2$—CO$_2$—NHS, are commonly used forms of activated carboxylic acid PEGs, and they are prepared by reacting carboxylic acid PEGs with N-hydroxysuccinimide.

PEG hydrogels, which are water-swollen gels, have been used for wound covering and drug delivery. PEG hydrogels are prepared by incorporating the soluble, hydrophilic polymer into a chemically crosslinked network or matrix so that addition of water produces an insoluble, swollen gel. Substances useful as drugs typically are not covalently attached to the PEG hydrogel for in vivo delivery. Instead, the substances are trapped within the crosslinked matrix and pass through the interstices in the matrix. The insoluble matrix can remain in the body indefinitely, and control of the release of the drug typically can be somewhat imprecise.

One approach to preparation of these hydrogels is described by Embrey and Grant in U.S. Pat. No. 4,894,238. The ends of the linear polymer are connected by various strong, nondegradable chemical linkages. For example, linear PEG is incorporated into a crosslinked network by reacting with a triol and a diisocyanate to form hydrolytically stable urethane linkages that are nondegradable in water.

A related approach for preparation of PEG hydrogels has been described by Gayet and Fortier in *J. Controlled Release*, 38, 177–184 (1996) in which linear PEG was activated as the p-nitrophenylcarbonate and crosslinked by reaction with a protein, bovine serum albumin. The linkages formed are hydrolytically stable urethane groups and the hydrogels are nondegradable in water.

In another approach, described by N. S. Chu in U.S. Pat. No. 3,963,805, nondegradable PEG networks have been prepared by random entanglement of PEG chains with other polymers formed by use of free radical initiators mixed with multifunctional monomers. P. A. King described nondegradable PEG hydrogels in U.S. Pat. No. 3,149,006 that have been prepared by radiation-induced crosslinking of high molecular weight PEG.

Nagaoka et al. described in U.S. Pat. No. 4,424,311 preparing PEG hydrogels by copolymerization of PEG methacrylate with other comonomers such as methyl methacrylate. Vinyl polymerization produces a polyethylene backbone with PEG attached. The methyl methacrylate comonomer is added to give the gel additional physical strength.

Sawhney et al. described, in *Macromolecules,* 26, 581 (1993) and U.S. Pat. No. 5,626,863, the preparation of block copolymers of polyglycolide or polylactide and PEG that are terminated with acrylate groups:

$$CH_2=CH-CO-(O-CHR-CO)_n-O-PEG-O-(CO-CHR-O)_n-OC-CH=CH_2$$

where R is $CH_3-$ or H.

In the above formula, the glycolide blocks are the $-OCH_2-CO-$ units; addition of a methyl group to the methylene group gives rise to a lactide block; n can be multiples of 2. Vinyl polymerization of the acrylate groups produces an insoluble, crosslinked gel with a polyethylene backbone. The polylactide or polyglycolide segments of the polymer backbone shown above, which are ester groups, are susceptible to slow hydrolytic breakdown, with the result that the crosslinked gel undergoes slow degradation and dissolution. While this approach provides for degradable hydrogels, the structure provides no possibility of covalently attaching proteins or other drugs to the hydrogel for controlled release. Applications of these hydrogels in drug delivery are thus restricted to release of proteins or other drugs physically entrapped within the hydrogel, thus reducing the potential for advantageous manipulation of release kinetics.

Hubbell, Pathak, Sawhney, Desai, and Hill (U.S. Pat. No. 5,410,016, 1995) polymerized:

$$\text{Protein-NH-PEG-O}_2\text{C}-\text{CH}=\text{CH2}$$

with long wavelength uv radiation to obtain a PEG acrylate polymer with a protein linked to it. The link between the PEG and the protein was not degradable, so the protein could only be hydrolytically released with PEG attached. Since the acrylate polymer is not hydrolytically degradable, the release of the PEG protein derivative is not controllable.

Yang, Mesiano, Venkatasubramanian, Gross, Harris and Russell in *J. Am. Chem. Soc.* 117, 4843–4850, (1995) described heterobifunctional poly(ethylene glycols) having an acrylate group on one terminus and an activated carboxylic acid on the second terminus. They demonstrated the attachment of this PEG derivative to a protein and incorporation of the resulting PEG protein derivative into an acrylate polymer. However, the PEG backbone there is not degradable and the protein was thus, in effect, permanently bound to the acrylate polymer.

SUMMARY OF THE INVENTION

This invention provides heterobifunctional acrylates of poly(alkylene oxides); especially poly(ethylene glycol) (PEG) acrylates having linkages that are hydrolytically degradable and conjugates prepared from these acrylates having target materials such as proteins covalently linked thereto. Hydrogels can also be prepared from these acrylates. The target materials can be released from the hydrogels through controllable hydrolytic degradation of the hydrogels.

In one embodiment of the invention, heterobifunctional PEG is provided which is represented by the formula:

$$CH_2=CZ-CO_2\text{-PEG-W-Q}$$

where Z is an alkyl group or hydrogen atom, W is a hydrolytically unstable linkage comprising a hydrolyzable covalent bond, and Q is a reactive moiety capable of reacting with a target to form a covalent linkage thus linking the PEG polymer to the target.

In another embodiment, this invention also provides a heterobifunctional PEG with a hydrolyzable linkage W in the PEG backbone and having an acrylate group at one terminus and a reactive moiety Q at the other terminus. The heterobifunctional PEG is represented by the formula of:

$$CH_2=CZ-CO_2\text{-PEG-W-PEG-Q}$$

where Z is an alkyl group or hydrogen atom, W is a hydrolytically unstable linkage comprising a hydrolyzable bond, and Q is a reactive moiety capable of reacting with a moiety on a target such as protein or a drug.

The present invention also encompasses a conjugate having a formula of:

$$(CH_2=CZ-CO_2\text{-PEG-W-L})_x\text{-T}$$

where Z and W are as described above, T is a target, e.g., a protein or a drug, L is a covalent linkage formed in the reaction between Q and a reactive moiety of T, and x is a number from 1 to 10.

In yet another embodiment of the invention, a conjugate of heterobifunctional PEG and a target is provided having the formula $$(CH_2=CZ-CO_2\text{-PEG-W-PEG-L})_x\text{-T}$$

where Z and W are as described above, T is a target, e.g., a protein or a drug, which is linked to the PEG polymer as a result of the reaction between the reactive moiety Q and a moiety on T, L is a covalent linkage formed in the reaction between Q and a reactive group of T, and x is a number of from 1 to 10.

This invention further provides polymers formed by vinyl polymerization of the aforementioned heterobifunctional PEG or conjugates thereof, represented by the formula: $CH_2=CZ\text{-}CO_2\text{-PEG-W-Q}$, $(CH_2=CZ\text{-}CO_2\text{-PEG-W-L})_x\text{-T}$, $CH_2=CZ\text{-}CO_2\text{-PEG-W-PEG-Q}$, and $(CH_2=CZ\text{-}CO_2\text{-PEG-W-PEG-L})_x\text{-T}$. The weak chemical linkages in the thus formed polymers provide for hydrolytic breakdown and concomitant release of bound target molecules. For example, polymerization of the above-mentioned conjugate:

$$(CH_2=CZ-CO_2\text{-PEG-W-PEG-L})_x\text{-T}$$

yields a water-soluble acrylate polymer which upon hydrolytic degradation liberates a smaller PEG fragment bearing a target such as a protein or a drug.

In another embodiment of the invention, hydrogels are formed by copolymerizing a heterobifunctional PEG conjugate of this invention with a PEG molecule having two or more acrylate groups ("PEG multiacrylate"). Exemplary examples of such PEG multiacrylate can be:

$$CH_2=CHCO_2\text{-PEG-O}_2CCH=CH_2$$

or $$CH_2=CHCO_2\text{-PEG-O}-CH_2CO_2CH(CH_3)$$
$$CH_2CONH\text{-PEGO}_2CCH=CH_2$$

The hydrogel of the present invention is a cross-linked network in which protein or other target molecules are covalently bound to a degradable matrix. Because of the hydrolytically unstable linkages W in the hydrogels, the target molecules such as drug or protein molecules can be released as a result of the breakdown of the unstable linkages.

In the heterobifunctional PEG, polymers, and hydrogels of the present invention, the hydrolytic breakdown of the hydrolytically unstable linkages W can be controlled in part by varying W, in particular the number of methylene group proximate to the hydrolyzable bond in W. Specifically, as the number of methylene group increases, the hydrolysis rate of the hydrolyzable bond of W decreases.

Further, in the hydrogel of the present invention, the release rate of the target from the hydrogel can also be controlled by varying the number x in the above formula of the PEG conjugate, i.e., the number of the PEG acrylate linked to the target. The release rate of the target from the hydrogel is decreased when the number of PEG acrylate linked to the target is increased, and vice versa.

Thus, the present invention provides heterbifunctional PEG and hydrogels formed therefrom having target molecules covalently linked to the hyrogels. In contrast to the PEG hydrogels known heretofore in the art, the target molecules can be released in a controlled fashion from the PEG hydrogels of the present invention. Further, since the release rate of the target can be determined by both the number of the attached PEG and the structure of the hydrolytically unstable linkage in the attached PEG, more precise control of the release kinetics is made possible. Therefore, suitable drug carriers for drug delivery which meet different drug release requirements can be made in accordance with the present invention.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

BRIEF DESCRIPTION OF THE DRAWINGS

FIG. 1 is a plot of the release profile of lucifer-yellow lysozyme from a PEG acrylate hydrogel.

DETAILED DESCRIPTION OF THE INVENTION

A heterobifunctional water soluble and hydrolytically degradable polymer is provided comprising a polymer backbone having a degradable linkage, a first terminus comprising an acrylate group, and a second terminus comprising a target or a functional group capable of coupling the polymer to a target.

As used herein, the terms "group," "moiety," "site," and "radical" are all somewhat synonymous and are used herein to refer to distinct, definable portions or units of a molecule or units that perform some function or activity or reactive with other molecules or portions of molecules.

The term "linkage" is used herein to refer to groups that normally are formed as the result of a chemical reaction and typically are covalent linkages. Hydrolytically stable linkages means that the linkages are stable in water and do not react with water at useful pHs for an extended period of time, potentially indefinitely. Hydrolytically unstable linkages are those that react with water, typically causing degradation of a hydrogel and release of substances trapped within the matrix. The linkage is said to be subject to hydrolysis and to be hydrolyzable. The time it takes to degrade the cross-linked polymeric structure is referred to as the rate of hydrolysis and is usually measured in terms of its half life. Thus, in the present invention, the target molecules typically are released at a predetermined rate or within a predetermined time.

"Heterobifunctional" refers to the first and second terminii on the polymer, one of which is acrylate, and the other of which is the target molecule or or functional group capable of coupling the polymer to a target.

A preferred embodiment of the heterobifunctional polymer is represented by the formula:

$CH_2=CZ\text{-}CO_2\text{-POLY-W-POLY'-Q}.$

Another preferred embodiment is represented by the formula:

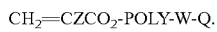

$CH_2=CZCO_2\text{-POLY-W-Q}.$

In the above formulas, Z can be H or an alkyl group. Preferably, the alkyl group has less than 20 carbon atoms, more preferably less than 10 carbon atoms, and most preferably less than 3 carbon atoms.

Typically, the polymer backbone represented by POLY and POLY' are poly(alkylene oxide), including derivatives thereof. A suitable poly(alkylene oxide) or derivative thereof can comprise a group represented by the formula $-(CH_2CHRO)_n-CH_2CHR-$ in which R is H or an alkyl group, and n ranges from about 10 to about 4000. Preferably, R is H and the polymer backbone comprises a poly(ethylene glycol) group. Poly(ethylene glycol) is preferred because it is substantially non-toxic and non-immunogenic.

W is a hydrolytically unstable linkage that can break down in an aqueous environment by hydrolysis. Typically, the linkage W comprises a hydrolyzable covalent bond. Suitable examples of such hydrolyzable covalent bonds include, but are not limited to, carboxylate esters, imines, phosphate esters, acetals, orthoesters, peptide bonds, and oligonucleotides.

These hydrolyzable bonds can be formed by reaction of pairs of reactive moieties, for example, alcohol and carboxylic acid reacting to form carboxylate esters, amine and aldehyde reacting to form imines, hydrazide and aldehyde reacting to form hydrazones, alcohol and phosphate reacting to form phosphate ester, aldehyde and alcohol reacting to from acetals, alcohols and formate reacting to form orthoesters, amino acid and amino acid reacting to form peptide bonds, nucleotide and nucleotide to form oligonucleotide bonds.

Typically the hydrolytically degradable linkage W further comprises a plurality of alkylene groups, preferably methylene groups, proximate to the hydrolyzable bond. The rate of degradation of the hydrolytically degradable linkage W by hydrolysis is in part determined by the number of the alkylene groups and the distance of these groups from the hydrolyzable bond.

In a preferred embodiment, W has the structure of:

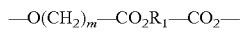

$-O(CH_2)_m-CO_2R_1-CO_2-$ or

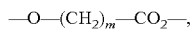

$-O-(CH_2)_m-CO_2-,$ where m ranges from 1 to 10 and $R_1$ is selected from the group consisting of $-CH_2-$, $-CH_2CH_2-$, and $-CH(CH_3)CH_2-$. In these two examples, the rate of hydrolysis of the ester linkage increases with a decreasing value of m.

In the heterobifunctional polymer of the above formula, Q is a reactive moiety capable of reacting with a reactive group in a target so as to form a linkage between the heterobifunctional polymer and the target. A target is defined below. Examples of Q include, but are not limited to, aldehydes, carboxylic acids, carbonate esters, hydrazides, N-succinimidyl esters, amines, isocyanates, alcohols, epoxide, thiols, orthopyridyl disulfides, and sulfonate esters.

Typically, Q reacts with a reactive group on a target to form a stable linkage such that the heterobifunctional polymer of the invention is conjugated onto a target. A conjugate formed in this manner can be represented by the formula:

$(CH_2=CZCO_2\text{-POLY-W-L})_x\text{-T}$ or $(CH_2=CZCO_2\text{-POLY-W-POLY'-L})_x\text{-T}$ where Z, POLY, POLY' and W are as described above. L represents a stable linkage formed as a result of the reaction between Q and a reactive group on T as described below. Examples of the hydrolytically stable linkage L include, but are not limited to, amide from the reaction of active esters with amine, urethane from the reaction of isocyanate with alcohol, urea from the reaction of isocyanate with amine, amine from the reaction of aldehyde with amine and a reducing agent, amine from the reaction of epoxide with amine, and sulfonamide from the reaction of sulfonate ester with amine.

T represents a target which is typically a molecule or an entity having a desirable function or property. For example, T can be a protein or a pharmaceutically effective agent. By forming a conjugate or hydrogel of the invention, a target T is in effect "loaded" onto a carrier and can be delivered into a desired location under the protection of the polymer backbone or the hydrogel matrix before it is released by hydrolytic breakdown of the unstable linkage W in the polymer or hydrogel.

Accordingly, a target T in this invention can be any substance to which it is desirable to link poly(alkylene oxide) or derivatives thereof. T must have a reactive group capable of reacting with the reactive moiety Q to form a stable linkage L. Examples of suitable Ts include, but are not limited to, proteins, carbohydrates, lipids, hormones, oligonucleotides. Typically, T is a pharmaceutically effective agent. Examples of such substances include, but are not limited to, antibodies and fragments thereof; cytokines including, but not limited to interleukins (e.g., IL-1, IL-2, IL-3, IL-4, IL-5, IL-6, IL-7, IL-8, IL-9, IL-10, IL-11, and derivatives or fragments thereof), interferons (e.g., IFN-alpha, IFN-beta and IFN-gamma); growth factors, including but not limited to colony stimulating factors, erythropoietins, haemopoietins, epidermal growth factors, platelet derived growth factors, transforming growth factors, amphiregulin, somatomedin-C, bone growth factor, fibroblast growth factors, insulin-like growth factors, heparin binding growth factors, tumor growth factors and other growth factors, platelet activating factors, macrophage activation factors, and other activating factors; transcription factors; substances affecting blood clotting including but not limited to heparin, proteases and their pro-factors, clotting factors VII, VIII, IX, X, XI and XII, antithrombin III, protein C, protein S, streptokinase, urokinase, prourokinase, tissue plasminogen activator, fibrinogen, hirudin, other fibrinolytic/anticoagulant agents and other coagulation factors; lipids including but not limited to phosphatidylethanolamine, phosphatidylserine, sphingosine, cholesterol and other steroids and derivatives thereof; nucleotides including but not limited to ribonucleotides, deoxyribonucleotides, nucleosides, oligonucleotides, DNA, and RNA; enzymes; vaccines; vitamins; antibiotics; and other pharmaceutically effective agents including but not limited to anthelminthic agents, noradrenalin, alpha adrenergic receptor ligands, dopamine receptor ligands, histamine receptor ligands, GABA/benzodiazepine receptor ligands, serotonin receptor ligands, leukotrienes and tri-iodothyronine and other small effector molecules, doxorubicin, methotrexate and other cytotoxic agents and derivatives thereof.

When the hydrolytically unstable linkage W is situated within the poly(alkylene oxide) backbone of the heterobifunctional polymers or the conjugates of this invention, W can be formed by reacting two modified polymers having terminal reactive moieties as illustrated below:

-PEG-X+Y-PEG- → -PEG-W-PEG-

In the above illustration, -W- represents the hydrolytically unstable weak linkage. X and Y represent the reactive moiety pairs as described above. Exemplary reactions are illustrated below where the reverse reactions illustrate hydrolytic reversibility:

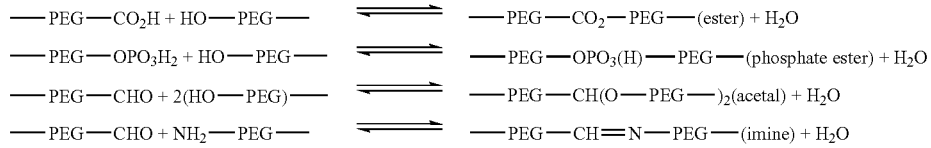

The hydrolytically stable linkage L can be formed, for example, through the following reaction:

-PEG-W-Q+U-T → -PEG-W-L-T or

-PEG-W-PEG-Q+U-T → -PEG-W-PEG-L-T where U is a reactive group on T.

The skilled artisan should recognize that when reference is made to an X moiety reacting with a Y moiety, or a Q group with a U group, additional reagents or steps may be employed according to commonly accepted chemical procedures and standards to achieve the desired linkage W or L as the case may be. There are many possible routes, too numerous to mention here, that could be taken and that should be readily apparent to the skilled artisan. For example, one of skill in the art can be expected to understand that when an alcohol and a carboxylic acid are reacted, the acid typically is converted to another form, the acid chloride, prior to reaction with alcohol. Several examples are demonstrated in the Examples below.

The heterobifunctional polymers and conjugates of this invention described above can be employed in polymerization reactions to form polymers and hydrogels.

Since the heterfunctional polymers and the conjugates of this invention all have an acrylate group, vinyl polymerization of each of the heterfunctional polymers or conjugates can be conducted by a method known in the art. Two or more compounds selected from the heterfunctional polymers and the conjugates of this invention can be copolymerized. Many methods of vinyl polymerization are generally known in the art and are useful in the present invention. Generally, when a conjugate is involved in the polymerization or copolymerization, conditions for the polymerization reaction should be selected such that the target in the conjugate is not adversely affected. Suitable polymerization methods include, for example, redox initiation and photo initiation. Other suitable methods should be apparent to a skilled artisan once apprised of the present disclosure.

In accordance with another aspect of this invention, hydrogels can be prepared from the heterobifunctional polymers and conjugates, as well as the vinyl polymers by polymerization and/or crosslinking. As used herein, "hydrogel" is intended to mean gels produced by incorporating the soluble hydrophilic polymers (e.g., heterfunctional polymers and conjugates of this invention) into a chemically crosslinked network or matrix so that addition of water produces an insoluble swollen gel. Crosslinks can be formed from the heterobifunctional polymers or conjugates themselves. However, typically, crosslinks are introduced by copolymerizing the heterobifunctional polymers or conjugates with a multiacrylate as a monomer. By "multiacrylate" it is intended to mean a molecule having two or more acrylate groups so that it can form a crosslinking bridge in vinyl polymerization of the heterobifunctional polymers or conjugates of the present invention. Preferably, the multiacrylate used is a PEG multiacrylate, i.e., a PEG molecule having two or more acrylate groups therein. Exemplary examples of such PEG multiacrylate can be, e.g.,

or

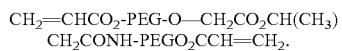

However, many other multiacrylate monomers can also be used as is apparent to a skilled artisan apprised of this invention.

Typically, a hydrolytically degradable conjugate of this invention having a target therein is used in preparing the hydrogel of this invention. In this manner, the target is incorporated covalently into the hydrogel which can be used as a carrier for in vivo delivery or other applications. Thus, the hydrogels of the invention are particularly useful in drug delivery systems. By "drug" is meant any substance intended for the diagnosis, cure, mitigation, treatment, or prevention of disease in humans and other animals, or to otherwise enhance physical or mental well being. For example, hydrogels made from the crosslinked PEG polymeric structures of the invention can be used for wound dressings. Wound dressings can be used internally to provide dressings that degrade within the body over time.

In the hydrogel of this invention, the target material that is covalently linked to the hydrogel can be released in an aqueous environment by hydrolytic breakdown of the hydrolytically unstable linkage W. In order to control the rate of release of the target in the hydrogel, the unstable linkage W can be manipulated during the preparation of the hydrogel. It has been discovered that the number of atoms, particularly alkylene groups, proximate to the hydrolyzable bond in W affects the hydrolysis rate of the hydrolyzable bond. For example, as the number of methylene group increases, the hydrolysis rate decreases.

For example, when W has the structure of:

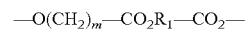

where m ranges from 1 to 10, $R_1$ is selected from the group consisting of $—CH_2—$, $—CH_2CH_2—$, and $—CH(CH_3)CH_2—$, increasing the m value decreases the hydrolysis rate of esters and increases the time required for the gel to degrade. Typically, if m in the above example is 1, then the ester linkages of the gel will hydrolyze with a half life of about 4 days at pH 7 and 37° C. If m is 2, then the half life of hydrolytic degradation of the ester linkages is about 43 days at pH 7 and 37° C. Phosphate esters, acetals, imines, and other hydrolytically unstable linkages can be similarly formed and the hydrolysis rate can be similarly controlled by controlling the number of methylene groups adjacent the hydrolytically unstable linkage.

In addition, in the hydrogel of the present invention, the release rate of the target from the hydrogel can also be controlled by varying the number x of the PEG acrylates linked to the target. The release rate of the target from the hydrogel is decreased when the number of PEG acrylates linked to the target is increased. Release rate is increased by decreasing the number.

In the hydrogel of this invention, a two-fold control of the target release rate is made possible: (1) by varying the number of atoms proximate to the hydrolyzable bond in the hydrolytically unstable linkage W; and (2) by controlling the number of the PEG acrylates linked to the target. As a result, the hydrogels of this invention can be designed to have a more precisely controlled target release rate, which is useful in hydrogel applications, e.g., drug delivery.

The following examples are given to illustrate the invention, but should not be considered in limitation of the invention.

Example 1. Synthesis of $CH_2$=$CHCO_2$-PEG-$OCH_2CO_2CH(CH_3)CH_2CO_2NS$ (NS=N-succinimidyl)

Example 2. Modification of proteins

Example 3. Preparation of gels

Example 4. Release of proteins from gels

EXAMPLES

Example 1

Preparation of $CH_2$=$CHCO_2$-PEG-$OCH_2CO_2CH(CH_3)CH_2CO_2NS$

Reaction scheme:

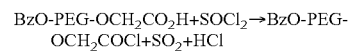

(Bz=Benzyl)

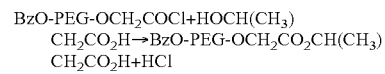

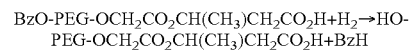

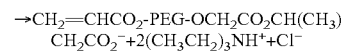

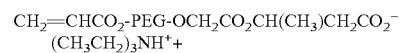

a.) Preparation of BzO-PEG-OCH$_2$CO$_2$—CH(CH$_3$)CH$_2$CO$_2$H

BzO-PEG-OCH$_2$CO$_2$H (MW=3400, 15 g, 4.4 mmole) was azeotropically dried with 60 ml of toluene under N$_2$. After two hours, the solution was slowly cooled to room temperature. To this solution was added thionyl chloride (18 ml, 36 mmole). The resulting solution was stirred overnight, the solvent condensed by rotary evaporation, and the syrup dried in vacuo for about four hours over P$_2$O$_5$ powder. 3-hydroxybutyric acid (1.45 g, 13.5 mmole) was azeotropically dried with 70 ml of 1,4-dioxane, and then added to the dried BzO-PEG-OCH$_2$COCl. After the PEG acyl chloride had dissolved, 4.5 ml of dry triethylamine was injected into the system and the solution was stirred overnight. The salt was removed by filtration and the filtrate was condensed on a rotary evaporator at 55° C. and dried in vacuo. The crude product was then dissolved in 100 ml of distilled water and the pH of the solution was adjusted to 3.0. The aqueous phase was extracted three times with a total of 80 ml of methylene chloride. The organic phase was dried over sodium sulfate, filtered, condensed on a rotary evaporator, and precipitated into 100 ml of ethyl ether. The product was collected by filtration and dried in vacuo at room temperature. Yield 14 g (93%). $^1$H nmr (DMSO-d$_6$): δ 3.5 (br m, PEG), 2.58 (d, -PEGCOOCH(CH$_3$)CH$_2$COOH), 5.14 (h, -PEG-COOCH(CH$_3$)CH$_2$COOH), 1.21 (d, -PEG-COOCH(CH$_3$)CH$_2$COOH), 4.055 (s, PEGOCH$_2$COO), 4.49 (s, $_c$6H$_5$—CH$_2$—OPEG-), 7.33 (s+comp. mult., C$_6$H$_5$—CH$_2$—OPEG-).

b.) Preparation of HO-PEG-OCH$_2$CO$_2$—CH(CH$_3$)CH$_2$CO$_2$H

A solution of BzO-PEG-OCH$_2$CO$_2$-PEG-OCH(CH$_3$)CH$_2$CO$_2$H (8 g) in benzene (50 ml) was hydrogenolyzed with H$_2$ (2 atm) on 4 gram Pd/C (10%) at room temperature for 48 hours. The catalyst was removed by filtration, the solvent was condensed, and the solution was precipitated into ethyl ether. The product was collected by filtration and dried in vacuo at room temperature.

Yield: 6.6 gram (83%). $^1$H nmr (DMSO-d$_6$): δ 3.5 (br m, PEG), 2.51 (d, -PEGCO$_2$CH(CH$_3$)CH$_2$CO$_2$H), 5.16 (h, -PEG-CO$_2$CH(CH$_3$)CH$_2$CO$_2$H), 1.22 (d, -PEG-CO$_2$CH(CH$_3$)CH$_2$CO$_2$H), 4.06 (s, -PEGOCH$_2$CO$_2$PEG-).

c.) Preparation of CH$_2$=CHCO$_2$-PEG-OCH$_2$CO$_2$—CH(CH$_3$)CH$_2$CO$_2$H

HO-PEG-OCH$_2$CO$_2$CH(CH$_3$)CH$_2$CO$_2$H (3 g, 0.88 mmole) was azeotropically distilled with 40 ml of toluene under N$_2$ until approximately 15 ml of solution remained. The solution was then cooled to room temperature under N$_2$ and 25 ml of methylene chloride and triethylamine (1.5 mmole) were added. The solution was cooled in an ice bath and acryloyl chloride (2 mmole) were added dropwise. After addition of acryloyl chloride, the ice bath was removed and the solution was stirred at room temperature overnight. The methylene chloride was then partially removed under vacuum, the salt was removed by filtration, and the filtrate added to 100 ml of ether. The precipitated product was collected by filtration and dried in vacuo. The product was then dissolved in sodium acetate buffer (0.1M, pH 5.5), stirred for half an hour, and extracted three times with methylene chloride. The organic phase was dried over sodium sulfate, filtered, condensed, and precipitated in 100 ml of ethyl ether. The precipitate was collected by filtration and dried in vacuo at room temperature. Yield 2.4 g (80%). $^1$H nmr (DMSO-d$_6$): δ 3.5 (br m, PEG), 2.51 (d, CH$_2$CO$_2$H), 5.16 (h, —CH(CH$_3$—), 1.22 (d, —CH(CH$_3$)—), 4.06 (s, PEGOCH$_2$CO$_2$PEG-), 4.21 (t, —CO$_2$CH$_2$CH$_2$O—), 5.85–6.45 (m, CH$_2$=CH—).

d.) Preparation of CH$_2$=CHCO$_2$-PEG-OCH$_2$CO$_2$—CH(CH$_3$)CH$_2$CO$_2$NS

CH$_2$=CH—CO$_2$-PEG-OCH$_2$CO$_2$CH(CH$_3$)CH$_2$CO$_2$H (1.4 g, approx. 0.4 mmole) and N-hydroxysuccinimide (51 mg, 0.43 mmole) was dissolved in 30 ml of dry methylene chloride. To this solution was added dicyclohexylcarbodiimide (95 mg, 0.45 mmole) in 5 ml of dry methylene chloride. The solution was stirred under nitrogen overnight and the solvent removed by rotary evaporation. The resulting syrup was dissolved in 10 ml of dry toluene and the insoluble solid was removed by filtration. The filtrate was added to 100 ml of dry ethyl ether and the precipitated product was collected by filtration and dried in vacuo at room temperature.

Yield 0.94 g (94%). $^1$H nmr (DMSO-d$_6$): δ 3.5 (br m, PEG), 3.0–3.2 (m, -PEGCOOCH(CH$_3$)CH$_2$COONS), 5.26 (h, PEGCOOCH(CH$_3$)CH$_2$COONS), 1.3 (d, -PEG-COOCH(CH$_3$)CH$_2$COONS), 4.10 (s, -PEGOCH$_2$COO (CM)), 2.81 (s, NS), 4.21 (t, CH$_2$=CH—COO—CH$_2$CH$_2$—O-PEG-, 4H), 5.85–6.45(m, CH$_2$=CHCOOPEG-).

Example 2

Modification of Proteins a) Modification of Lucifer-yellow Modified Lysozyme

CH$_2$=CHCO$_2$-PEG-OCH$_2$CO$_2$—CH(CH$_3$)CH$_2$CO$_2$NS (19 mg, 5.5 mmole) was dissolved in 0.1 ml of water and 0.5 ml of lucifer-yellow modified lysozyme solution and (20 mg/ml) in borate buffer (0.1M, pH 8.0) was added. The solution was shaken gently on an auto-shaker at room temperature for 3 hours. Completion of the reaction was demonstrated by capillary electrophoresis. The solution was then stored at 4° C. prior to release studies.

b) Modification of Fluorescein Isothiocyanate-Bovine Serum Albumin (FTIC-BSA):

CH$_2$=CHCO$_2$-PEG-OCH$_2$CO$_2$—CH(CH$_3$)CH$_2$CO$_2$NS (9.3 mg, 2.7 mmole) was dissolved in 0.5 ml of deionized water and 1.5 ml of FITC-BSA solution (15 mg/ml) in boric buffer (0.1M, pH 8.0) was added. The solution was shaken gently on an auto-shaker at room temperature for 3 hours. Completion of the reaction was demonstrated by capillary electrophoresis. The solution was then stored at 4° C. prior to release studies.

Example 3

Preparation of Gels a.) By Redox Initiation

A solution of (0.5 ml, 200 mg/ml in water of CH$_2$=CHCO$_2$-PEG-O—CH$_2$CO$_2$CH(CH$_3$)CH$_2$CONH-PEGO$_2$CCH=CH$_2$ or CH$_2$=CHCO$_2$-PEG-O—CH$_2$CO$_2$PEG-O$_2$CCH=CH$_2$, and 0.5 ml of buffered PEG acrylate-modified lucifer yellow lysozyme (Example 2a) solution (10 mg/ml, f and 20 ml of potassium persulfate (K$_2$S$_2$O$_8$, 100 mM) were mixed. To the solution was added 20 ml of iron sulfate (FeSO$_4$, 100 mM). After rapid shaking, a gel formed in a few minutes.

A suitable buffer for this procedure is boric buffer (0.1 M) or phosphate buffer (<0.01M) with pH range of 6 to 8.

b.) By Photo Initiation

Difunctional PEG Acrylate Solution (0.5 ml, 400 mg/ml in water, $CH_2$=$CHCO_2$-PEG-O 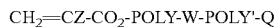 $CH_2CO_2CH(CH_3)$ $CH_2CONH$-$PEGO_2CCH$=$CH_2$ or $CH_2$=$CHCO_2$-PEG-O—$CH_2CO_2$PEG—$O_2CCH$=$CH_2$, 0.5 ml of buffered (pH 7) PEG acrylate-modified FTIC-BSA solution (Example 2b) and 100 ml of 2,2-dimethoxy-2-phenyl-acetophone solution (10 mg/ml in ethanol) were mixed. The solution was exposed to UV radiation at a wavelength of 360 nm and the gel formed in about 10 minutes.

Example 4

Release of Proteins from the Gels

The release of lucifer yellow lysozyme was monitored using a flow UV spectrophotometer at 428 nm and 37° C. in 0.1 M phosphate buffer (pH 7). Release profiles for two experiments are shown in FIG. 1.

Although the foregoing invention has been described in some detail by way of illustration and example for purposes of clarity of understanding, it will be obvious that certain changes and modifications may be practiced within the scope of the appended claims.

The invention claimed is:

1. A compound represented by the formula:

$CH_2$=CZ-$CO_2$-POLY-W-POLY'-Q where

Z represents H or alkyl;

POLY and POLY' are poly(alkylene oxide) groups that can be the same or different and are represented by the formula —$(CH_2CHRO)_n$—$CH_2CHR$— in which R is H or alkyl, and n ranges from about 10 to about 4000;

Q represents a functional group; and

W represents a hydrolytically unstable linkage selected from

—O$(CH_2)_m$—$CO_2R_1$—$CO_2$—, and 

—O—$(CH_2)_m$—$CO_2$— 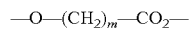

where m ranges from 1 to 10, and $R_1$ is —$CH_2$—, —$CH_2CH_2$— or —$CH(CH_3)CH_2$—.

2. The compound of claim 1, wherein Q is selected from the group consisting of aldehydes, carboxylic acids, carbonate esters, N-succinimidyl esters, sulfonate esters, amines, hydrazides, orthopyridyl disulfides, thiols, isocyanates, alcohols, and epoxide.

3. A compound represented by the formula:

$CH_2$=CZ-$CO_2$-POLY-W-POLY'-Q where

Z represents H or alkyl;

POLY and POLY' are poly(ethylene glycol) groups represented by the formula —$(CH_2CH_2O)_n$—$CH_2CH_2O$— in which n ranges from about 10 to about 4000;

Q represents a functional group; and

W represents a hydrolytically unstable linkage selected from

—O$(CH_2)_m$—$CO_2R_1$—$CO_2$—, and 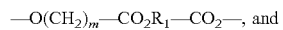

—O—$(CH_2)_m$—$CO_2$— 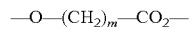

where m ranges from 1 to 10, and $R_1$ is —$CH_2$—, —$CH_2CH_2$— or —$CH(CH_3)CH_2$—.

4. The compound of claim 3, wherein Q is selected from the group consisting of aldehydes, carboxylic acids, sulfonate esters, amines, hydrazides, orthopyridyl disulfides, thiols, carbonate esters, N-succinimidyl esters, isocyanates, alcohols, and epoxide.

* * * * *